(12) United States Patent
Vij (10) Patent No.: US 9,383,421 B2
(45) Date of Patent: Jul. 5, 2016

(54) INTRA-BODY MEDICAL DEVICES FOR USE IN MRI ENVIRONMENTS

(71) Applicant: MRI Interventions, Inc., Memphis, TN (US)

(72) Inventor: Kamal Vij, Chandler, AZ (US)

(73) Assignee: MRI Interventions, Inc., Irvine, CA (US)

( * ) Notice: Subject to any disclaimer, the term of this patent is extended or adjusted under 35 U.S.C. 154(b) by 735 days.

(21) Appl. No.: 13/796,485

(22) Filed: Mar. 12, 2013

(65) Prior Publication Data

US 2014/0266205 A1    Sep. 18, 2014

(51) Int. Cl.

| G01R 33/28 | (2006.01) |
|---|---|
| A61B 5/00 | (2006.01) |
| A61B 5/055 | (2006.01) |
| A61B 5/06 | (2006.01) |
| A61B 18/14 | (2006.01) |
| A61B 18/00 | (2006.01) |
| A61B 17/00 | (2006.01) |

(52) U.S. Cl.
CPC .............. *G01R 33/287* (2013.01); *A61B 5/055* (2013.01); *A61B 5/062* (2013.01); *A61B 5/6852* (2013.01); *A61B 18/1492* (2013.01); *A61B 2017/00088* (2013.01); *A61B 2018/00577* (2013.01); *A61B 2562/043* (2013.01)

(58) Field of Classification Search
CPC .............................. G01R 33/287; A61B 5/055
See application file for complete search history.

(56) References Cited

U.S. PATENT DOCUMENTS

| 4,859,950 A | 8/1989 | Keren |
|---|---|---|
| 6,284,971 B1 | 9/2001 | Atalar et al. |
| 7,215,121 B2 | 5/2007 | Sambandamurthy et al. |
| 2010/0312096 A1* | 12/2010 | Guttman ................ A61B 5/418 600/411 |
| 2010/0317962 A1* | 12/2010 | Jenkins .................. A61B 5/055 600/411 |

* cited by examiner

*Primary Examiner* — Peter Luong
(74) *Attorney, Agent, or Firm* — Myers Bigel & Sibley (57) ABSTRACT

An MRI-compatible intrabody device includes an elongated flexible shaft having a distal end portion, an opposite proximal end portion, an electrical connector interface configured to be in electrical communication with an MRI scanner, and a tracking coil assembly adjacent the shaft distal end portion. The tracking coil assembly includes a first spool having opposing first and second end walls and a second spool having opposing third and fourth end walls. The second spool is in end-to-end relationship with the first spool such that the second and third end walls are in adjacent, spaced-apart relationship. A tracking coil is wound around the first spool, and a coaxial cable is wound around the second spool. An outer conductor of the coaxial cable is connected to one end of the tracking coil and the inner conductor of the coaxial cable is connected to an opposite end of the tracking coil.

10 Claims, 9 Drawing Sheets

INTRA-BODY MEDICAL DEVICES FOR USE IN MRI ENVIRONMENTS

FIELD OF THE INVENTION

The present invention relates generally to medical devices and, more particularly, to MRI-guided medical devices.

BACKGROUND

Numerous diagnostic and therapeutic procedures have been developed in which a catheter is translumninally advanced within a guide sheath or over a guidewire into various locations of a patient, such as the heart. These procedures conventionally have been conducted using X-ray and/or ultrasound imaging technology to facilitate guidance of the catheter through the body and to the target location. Unfortunately, X-ray imaging technology has a number of limitations, including limited anatomical visualization of the body and blood vessels, limited ability to obtain a cross-sectional view of a target vessel, and exposure of the subject to potentially damaging x-ray radiation.

Magnetic Resonance Imaging (MRI) technology has the potential to overcome these deficiencies. MRI has several distinct advantages over X-ray imaging technology, such as excellent soft-tissue contrast, the ability to define any tomographic plane, and the absence of ionizing radiation exposure. In addition, MRI offers several specific advantages that make it especially well suited for guiding various devices used in diagnostic and therapeutic procedures including: 1) real-time interactive imaging, 2) direct visualization of critical anatomic landmarks, 3) direct high resolution imaging, 4) visualization of a device-tissue interface, 5) the ability to actively track device position in three-dimensional space, and 6) elimination of radiation exposure.

Induced RF currents (referred to as RF coupling) on coaxial cables, electrical leads, guide wires, and other elongated devices utilized in MRI environments can be problematic. Such RE coupling may cause significant image artifacts, and may induce undesired heating and cause local tissue damage. To reduce the risk of tissue damage, it is desirable to reduce or prevent patient contact with cables and other conductive devices in an MRI environment. Such contact, however, may be unavoidable in some cases. For devices that are inserted inside the body, such as endorectal, esophageal, and intravascular devices, the risk of tissue damage may increase.

Various ways of limiting RF coupling have been proposed. For example, U.S. Pat. No. 7,215,121 describes a balun arrangement for use with an MR apparatus. U.S. Pat. No. 6,284,971 describes a coaxial cable adapted to resist undesired heating due to induced RF currents. U.S. Pat. No. 4,859,950 describes a balun circuit arrangement for RF coils in MR systems which addresses the adverse effects of induced currents in the cable system used for coupling the MR coils to the RF power transmitting and receiving equipment of the system. However, there remains a need for improved ways of reducing RF coupling in MRI environments.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, an MRI-compatible intrabody device includes an elongated flexible shaft having a distal end portion, and an opposite proximal end portion. The device includes an electrical connector interface that is configured to be in electrical communication with an MRI scanner. In some embodiments, the electrical connector interface may be located within a handle connected to the shaft proximal end portion.

At least one RF tracking coil is positioned adjacent the distal end portion of the shaft. A conductive lead, such as a coaxial cable, extends between the at least one RF tracking coil and the electrical connector interface and electrically connects the at least one tracking coil to an MRI scanner. In some embodiments, the conductive lead has a length sufficient to define an odd harmonic/multiple of a quarter wavelength of the operational frequency of the MRI Scanner. The at least one RF tracking coil is electrically connected to a circuit that reduces RF coupling when the at least one RF tracking coil is exposed to an MRI environment. In addition, in some embodiments, the conductive lead may include a series of back and forth segments along its length to resist undesired heating due to induced RF currents. In some embodiments, the conductive lead has a length sufficient to define an odd harmonic/multiple of a quarter wavelength of an operational frequency of the MRI Scanner.

In some embodiments, the at least one RF tracking coil is recessed within the catheter shaft and a layer of MRI-compatible material overlies the at least one RF tracking coil so as to be substantially flush with an outer surface of the shaft.

According to some embodiments of the present invention, a tracking coil assembly for use with an intrabody medical device includes a first MRI-compatible spool having opposing first and second end walls and a second MRI-compatible spool having opposing third and fourth end walls. The second spool is in end-to-end relationship with the first spool such that the second and third end walls are in adjacent, spaced-apart relationship. An MRI-compatible spacer may be positioned between the first and second spools to maintain a desired separation therebetween. A tracking coil is wound around the first spool between the opposing first and second end walls, and a coaxial cable is wound around the second spool. A free end of the coaxial cable extends through respective apertures in the second and third end walls, and the outer conductor of the coaxial cable is connected to one end of the tracking coil and the inner conductor of the coaxial cable is connected to an opposite end of the tracking coil.

In some embodiments, a distance between the first and second walls of the first spool is between about 0.25 mm and about 4 mm to accommodate various size tracking coils. In some embodiments, the tracking coil may be a 1-10 turn solenoid coil. In some embodiments, the coaxial cable is wound at least about twenty (20) times around the second spool. For example, the coaxial cable can be wound around the second spool between about twenty (20) times and one-hundred (100) times, and any range therebetween. However, embodiments of the present invention are not limited to a particular number of turns for either the tracking coil or the coaxial cable. In some embodiments, the tracking coil assembly is configured to be utilized within devices having a size that is between about 5 French to about 12 French.

An intrabody medical device may include a plurality of the tracking coil assemblies within a shaft thereof, wherein each tracking coil assembly is associated with a respective tracking coil. The intrabody medical device shaft may have a size that is between about 5 French to about 12 French.

According to some embodiments of the present invention, an MRI-compatible intrabody device includes an elongated flexible shaft having a distal end portion, and an opposite proximal end portion. A handle is attached to the proximal end portion, and includes an electrical connector interface configured to be in electrical communication with an MRI scanner. A pull wire extends through a lumen of the shaft and has a distal end and an opposite proximal end. The pull wire distal end is attached to the shaft distal end portion and the pull wire proximal end is attached to an actuator associated with the handle. Manipulation of the actuator causes movement of the pull wire which, in turn, causes articulation of the shaft distal end portion. A detector is associated with the handle and is configured to monitor movement or position of the pull wire and provide pull wire position data to a processor in communication with the MRI scanner via the electrical connector interface. In some embodiments, the detector is an optical detector that monitors movement of a plurality of markers on the pull wire as the actuator is manipulated. In some embodiments, the actuator is a piston that is movably secured to the handle and that is movable between extended and retracted positions relative the handle. The pull wire proximal end is attached to the piston. Movement of the piston causes articulation of the shaft distal end portion.

Embodiments of the present invention can be utilized in various applications where MRI is utilized. Exemplary applications include, but are not limited to, drug delivery procedures, neurological applications, cardiac applications (e.g., MRI-guided ablation procedures, etc.), other internal body applications (e.g., spinal, urethral, etc.), as well as external body applications. RF shields according to embodiments of the present invention are advantageous because they can have a very low profile allowing use in very small medical devices (e.g., devices having a size of between about 5 French and 12 French).

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate some exemplary embodiments. The drawings and description together serve to fully explain the exemplary embodiments.

DETAILED DESCRIPTION

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary by +/− twenty percent (20%).

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The terms "MRI or MR Scanner" are used interchangeably to refer to a Magnetic Resonance Imaging system and includes the magnet, the operating components, e.g., RF amplifier, gradient amplifiers and processors that direct the pulse sequences and select the scan planes. Embodiments of the present invention can be utilized with any MRI Scanner including, but not limited to, GE Healthcare: Signa 1.5 T/3.0 T; Philips Medical Systems: Achieva 1.5 T/3.0 T; Integra 1.5 T; Siemens: MAGNETOM Avanto; MAGNETOM Espree; MAGNETOM Symphony; MAGNETOM Trio; and MAGNETOM Verio.

The term "RF safe" means that a device and any conductive lead is configured to operate safely when exposed to RF signals, particularly RF signals associated with MRI systems, without inducing unplanned current that inadvertently unduly heats local tissue or interferes with the planned therapy.

The term "MRI visible" means that a device or portion thereof is visible, directly or indirectly, in an MRI image. The visibility may be indicated by the increased signal-to-noise ratio (SNR) of the MRI signal proximate the device or a lack of signal at the device. When MRI-visible, a device can act as an MRI receive antenna to collect signal from local tissue and/or the device actually generates MRI signal itself, such as via suitable medical grade hydro-based coatings, fluid (e.g., aqueous fluid) filled channels or lumens.

The term "MRI compatible" means that a component is safe for use in an MRI environment and as such is typically made of non-ferromagnetic MRI compatible material(s) suitable to reside and/or operate in a high magnetic field environment.

The term "high-magnetic field" refers to field strengths above about 0.5 T (Tesla), typically above 1.0 T, and more typically between about 1.5 T and 10 T. Embodiments of the invention may be particularly suitable for 1.5 T and/or 3.0 T systems.

The term "conductive lead" refers to an elongate assembly that includes one or more conductors. The lead typically connects two spaced apart components, such as, for example, a power source and/or input at one end portion and an electrode, tracking coil, and/or sensor at another position, such as at a distal end portion. The lead is typically flexible. The lead can be substantially tubular with a cylindrical shape, although other shapes may be used. The lead can have a solid or hollow body and may optionally include one or more lumens. In particular embodiments, a lead can be a relatively long implantable lead having a physical length of greater than about 10 cm (up to, for example, 1 m or even longer). The term "physical length" refers to a length that and can be measured in units of length or distance, e.g., millimeters, inches and the like, and is typically constant and does not vary when exposed to different electromagnetic fields (unlike electrical wavelengths), recognizing that a physical length may shrink or expand when exposed to low or high temperatures. The lead can include at least one electrode, and in some embodiments, a plurality of electrodes (which may be both on proximal and distal end portions), and in some particular embodiments, at least one electrode can be a recording or sensing electrode or both a recording and stimulating and/or ablating electrode. Examples of such leads include guidewires and/or interventional leads such as, for example, implantable pacemaker leads, spinal cord stimulator leads, deep brain stimulator leads, electrophysiology or other cardiac leads, leads used for implanted monitors, and leads used to administer a therapy during a surgical procedure.

The term "intrabody device" is used broadly to refer to any diagnostic or therapeutic medical device including, for example, catheters, needles (e.g., injection, suture, and biopsy), forceps (miniature), knives or other cutting members, ablation or stimulation probes, injection or other fluid delivery cannulas, mapping or optical probes or catheters, sheaths, guidewires, fiberscopes, dilators, scissors, implant material delivery cannulas or barrels, and the like, typically having a size that is between about 5 French to about 12 French, but other sizes may be appropriate.

The term "tracking member", as used herein, includes all types of components that are visible in an MRI image including miniature RF tracking coils, passive markers, and receive antennas. In some embodiments of the present invention a miniature RF tracking coil can be connected to a channel of an MRI Scanner. The MR Scanner can be configured to operate to interleave the data acquisition of the tracking coils with the image data acquisition. The tracking data is acquired in a 'tracking sequence block' which takes about 10 msec (or less). In some embodiments, the tracking sequence block can be executed between each acquisition of image data (the 'imaging sequence block'). So the tracking coil coordinates can be updated immediately before each image acquisition and at the same rate. The tracking sequence can give the coordinates of all tracking coils simultaneously. So, typically, the number of coils used to track a device has substantially no impact on the time required to track them.

Tuning Circuit for Tracking Coils

Figure 1:
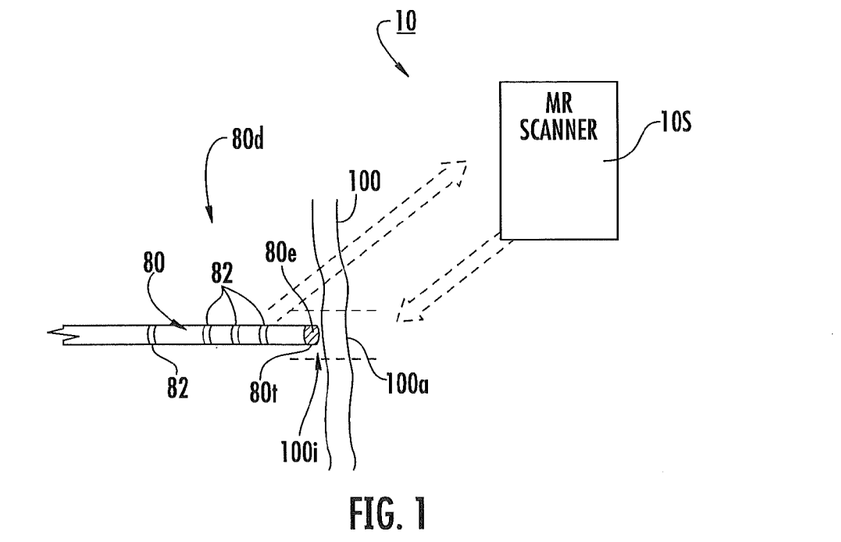
FIG. 1 is a schematic illustration of an MRI-guided system configured to show a device-tissue interface using near RT MRI data according to some embodiments of the present invention.
Figure 2:
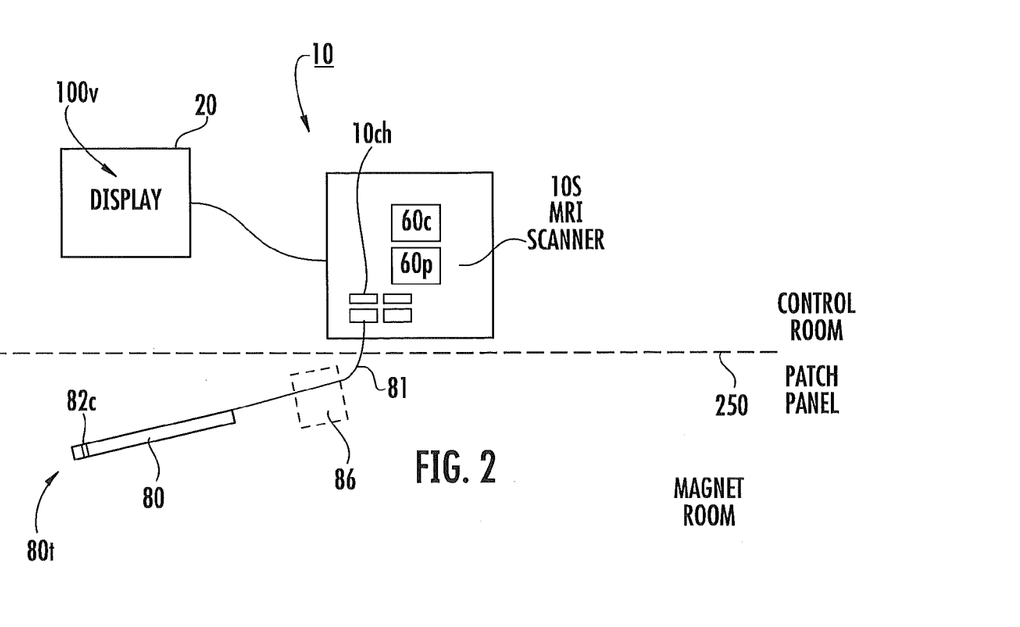
FIG. 2 is a schematic illustration of an intrabody device with a tracking coil electrically connected to a Scanner channel according to some embodiments of the present invention.

FIGS. 1 and 2 illustrate an MRI interventional system 10 with a scanner 10S and a (typically flexible) intrabody medical device 80 proximate target tissue 100 at a device-tissue interface 100*i*. The system 10 can be configured to electronically track the 3-D location of the device 80 in the body and identify and/or "know" the location of the tip portion 80*t* of the device 80 (e.g., the ablation or needle tip) in a coordinate system associated with the 3-D MRI imaging space.

As shown in FIG. 1, the device 80 can include a plurality of spaced apart tracking members 82 on a distal end portion thereof. In a particular embodiment, the device 80 can be an ablation catheter and the distal end portion 80*d*, typically tip 80*t*, can include an electrode 80*e* (typically at least one at a distal end portion of the device). Where used, the electrode 80e can be either or both a sensing and ablation electrode. A thermistor or thermocouple may be included to monitor temperature at and/or adjacent to the electrode 80e during ablation and/or at other times. The tracking members 82 can comprise miniature RF tracking coils, passive markers and/or a receive antenna. In some embodiments, the tracking members 82 include at least one miniature tracking coil 82c that is connected to a channel 10ch (FIG. 2) of an MRI Scanner 10S.

FIG. 2 illustrates that the device 80 can include at least one conductor 81, such as a coaxial cable that connects a respective tracking coil 82c to a channel 10ch of the MR Scanner 10S. The MR Scanner 10S can include at least 16 separate channels, and typically more channels but may operate with less as well. Each device 80 can include between about 1-10 tracking coils, typically between about 2-6. The coils 82c on a particular device 80 can be arranged with different numbers of turns, different dimensional spacing between adjacent coils 82c (where more than one coil is used) and/or other configurations. The circuit 60c can be configured to generate the device renderings based on tracking coil locations/positions relative to one another on a known device with a known shape and/or geometry or predictable or known changeable (deflectable) shape or form (e.g., deflectable end portion). The circuit 60c can identify or calculate the actual shape and orientation of the device for the renderings based on data from a CAD (computer aided design) model of the physical device. The circuit 60c can include data regarding known or predictable shape behavior based on forces applied to the device by the body or by internal or external components and/or based on the positions of the different tracking coils in 3-D image space and known relative (dimensional) spacings. Exemplary MRI-guided interventional systems that include such a circuit are described in co-owned U.S. Patent Application Publication No. 2010/0312096, which is incorporated herein by reference in its entirety.

Figure 3:
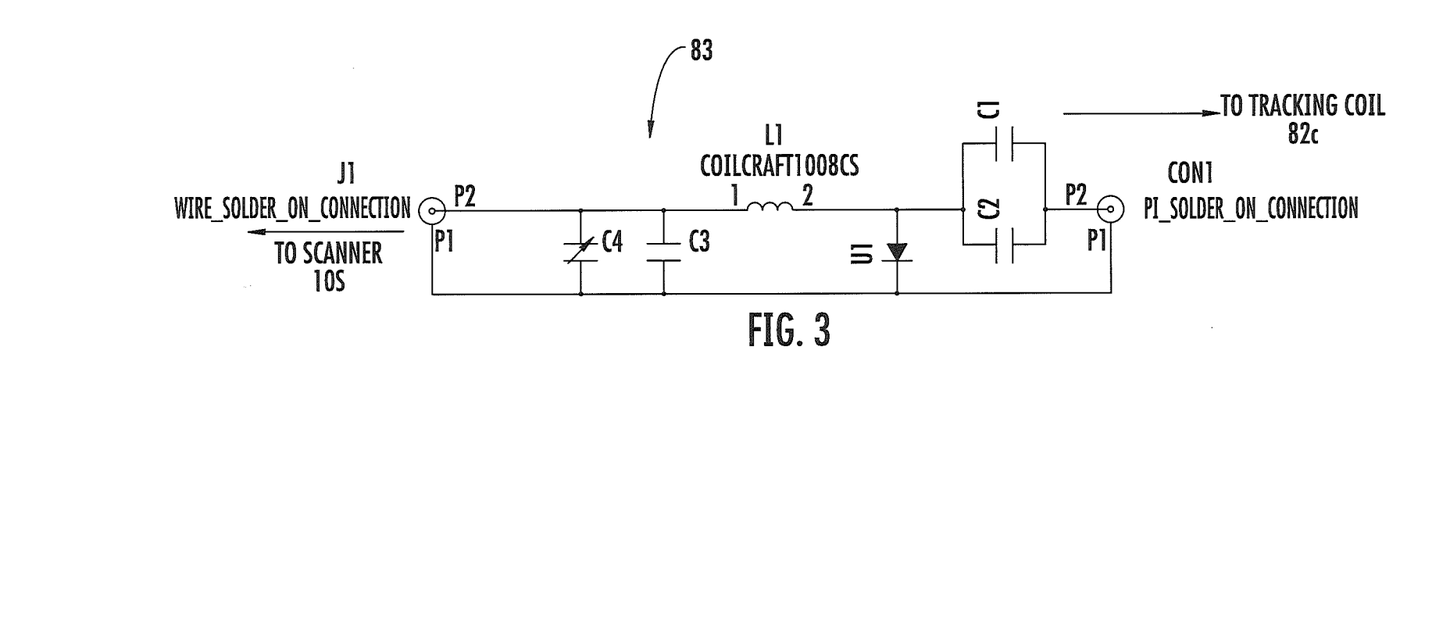
FIG. 3 is a circuit diagram of an exemplary tracking coil tuning circuit according to some embodiments of the present invention.

The tracking coils 82c can each include a tuning circuit 83 that can help stabilize the tracking signal for faster system identification of spatial coordinates. FIG. 3 illustrates an example of a tuning circuit 83 that may be particularly suitable for a tracking coil 82c on an intrabody medical device 80. As shown, CON1 connects the coaxial cable to the tracking coil 82c on a distal end portion of the device 80 while J1 connects to the MR Scanner channel 10ch. The Scanner 10S sends a DC bias to the circuit 83 and turns U1 diode "ON" to create an electrical short which creates a high impedance (open circuit) on the tracking coil to prevent current flow on the tracking coil and/or better tracking signal (stability). The tuning circuit 83 can be configured to have a 50 Ohm matching circuit (narrow band to Scanner frequency) to electrically connect the cable to the respective MR Scanner channel. When the diode U1 is open, the tracking coil data can be transmitted to the MR Scanner receiver channel 10ch. The C1 and C2 capacitors are large DC blocking capacitors. C4 is optional but can allow for fine tuning (typically between about 2-12 picofarads) to account for variability (tolerance) in components. It is contemplated that other tuning circuits and/or tracking signal stabilizer configurations can be used. The tuning circuit 83 can reside in the intrabody device 80 (such as in a handle or external portion), in a connector that connects the coil 82c to the respective MRI scanner channel 10ch, in the Scanner 10S, in an interface box 86 (FIG. 2), a patch panel 250 (FIG. 2) and/or the circuit 83 can be distributed among two or more of these or other components.

In some embodiments, each tracking coil 82c can be connected to a coaxial cable 81 having a length to the diode U1 via a proximal circuit board (which can hold the tuning circuit and/or a decoupling/matching circuit) sufficient to define a defined odd harmonic/multiple of a quarter wavelength at the operational frequency of the MRI Scanner 10S, e.g., λ/4, 3λ/4, 5λ/4, 7λ/4 at about 123.3 MHz for a 3.0 T MRI Scanner. This length may also help stabilize the tracking signal for more precise and speedy localization. The tuned RF coils can provide stable tracking signals for precise localization, typically within about 1 mm or less. Where a plurality (e.g., two closely spaced) adjacent tracking coils are fixed on a substantially rigid material, the tuned RF tracking coils 82c can provide a substantially constant spatial difference with respect to the corresponding tracking position signals.

Dephasing Excitation Pulse Sequence

The tracking sequence used in the system 10 can intentionally dephase signal perpendicular to the read-out direction to attenuate unwanted signals from 1) bulk objects and 2) regions sensed by other signal sensitive parts of the device 80 (FIGS. 1 and 2) which couple to the tracking coil 82c (e.g. the coaxial cable along the catheter shaft). This tends to leave only a sharp peak indicating the position of the tracking coil.

The tracking sequence block can include or consist of a plurality of (typically about three) repetitions of a small flip-angle excitation. Each repetition is designed to indicate the x, y or z component of the tracking coil coordinates in succession. Frequency encoding is used along the x-direction to obtain the x-coordinate, the y-direction for the y-coordinate, and the z-direction for the z-coordinate. When the frequency encoding is in the x-direction, the other two directions (y and z) are not spatially encoded, producing projection (spatially integrated) signals in those directions from all excitation regions. The dephasing gradient attempts to attenuate unwanted signals included in these projections. Once the tracking sequence block is complete, a spoiler gradient can be used to dephase any transverse signal remaining from the tracking before the imaging sequence block is executed.

Tracking Coil Recessed within Catheter Wall and Removable Tip

Figure 4A:
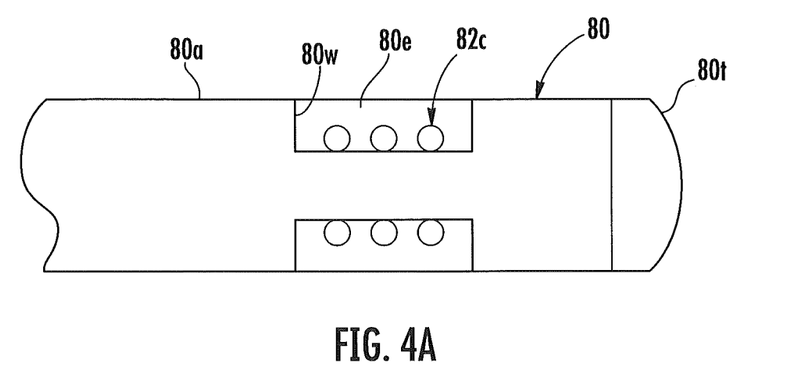
FIGS. 4A-4B are side section views of a portion of an intrabody device having a tracking coil recessed within a wall thereof, according to some embodiments of the present invention.
Figure 4B:
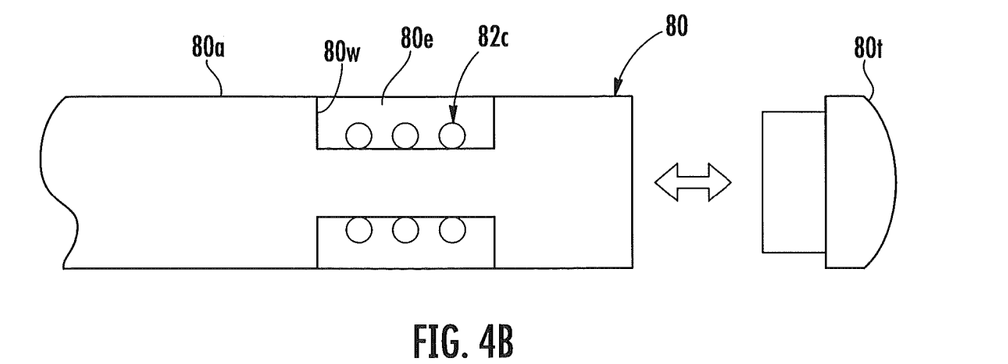

Referring to FIGS. 4A-4B, a tracking coil 82c may be recessed within the wall 80w of an intrabody medical device 80. The radial depth of the coil 82c within the device wall 80w may be such that the coil 82c is substantially flush with the outer surface 80a of the device 80. In other embodiments, the radial depth of the coil 82c within the device wall 80w may be such that the coil 82c is recessed with respect to the outer surface 80a of the device 80, as illustrated in FIGS. 4A-4B.

In some embodiments, the recessed tracking coil 80c may be covered with a layer of MRI-compatible material 80e such as, for example, a layer of polymeric material, epoxy, heat shrink material, etc. In the illustrated embodiment, the coil 80c is recessed within the device wall 80w such that the layer of material 80e overlying the coil 80c is substantially flush with the outer surface 80a of the device 80. However, embodiments of the present invention do not require the layer of material 80e to be flush with the outer surface 80a of the device 80. The layer of material 80e can be configured such that it extends outwardly slightly from the outer surface 80a of the device 80 or can be configured such that it is slightly recessed relative to the outer surface 80a of the device 80.

In the illustrated embodiment of FIGS. 4A-4B, the device 80 is an ablation catheter having a removable ablation tip 80t. The ablation tip 80t includes an electrode (not shown) that is connected to an RF lead (not shown) that extends longitudinally within a lumen of the device 80 to an electrical connector interface that connects the ablation electrode to an RF generator, as would be understood by one skilled in the art. The RF ablation electrode is formed from a conductive material capable of receiving RF energy and ablating tissue.

Exemplary materials include copper, as well as bio-compatible, MRI-compatible materials such as platinum, etc.

Coaxial Balun Embodiments

Figure 5:
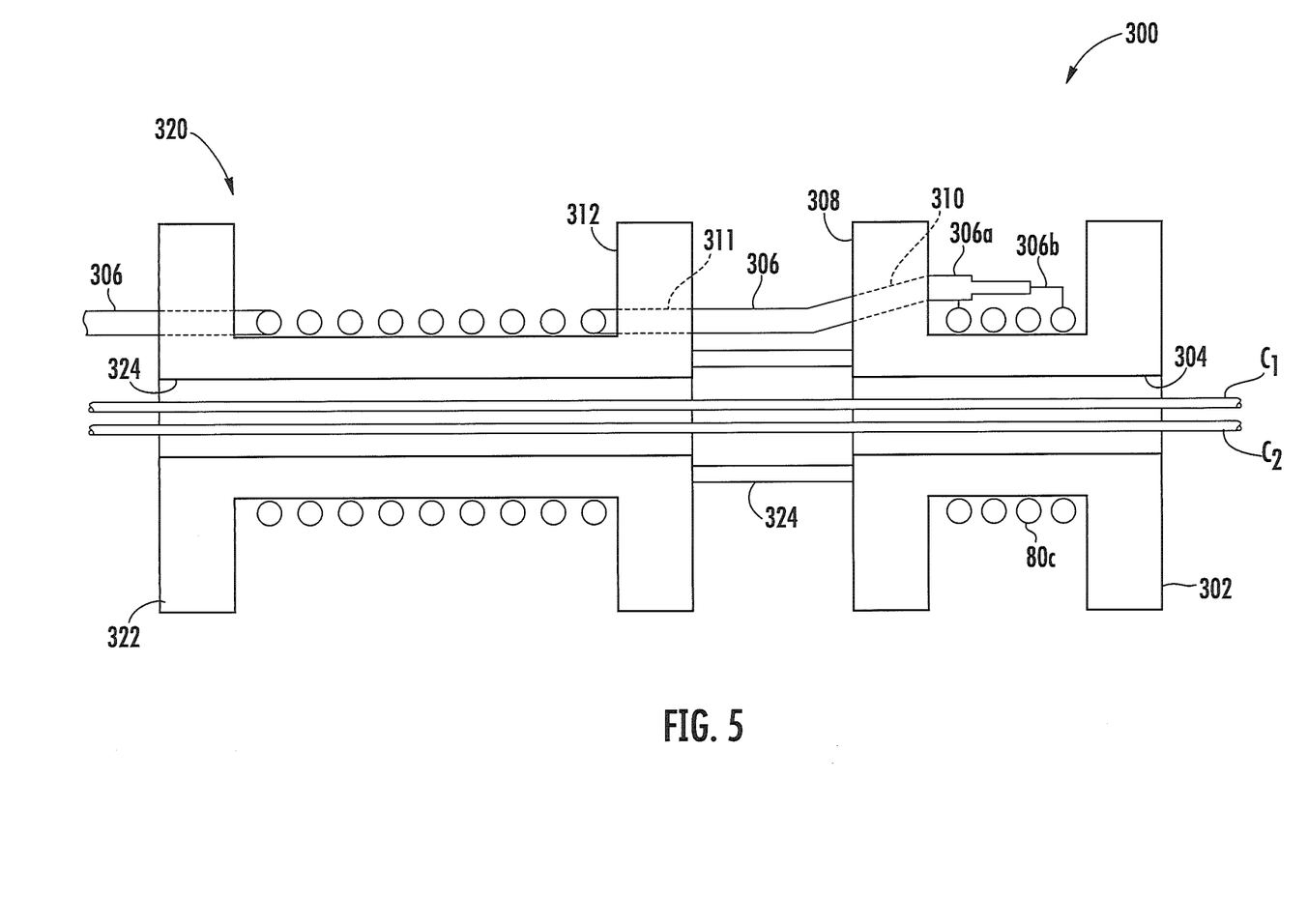
FIG. 5 is a side section view of a tracking coil assembly for use with an intrabody medical device, according to some embodiments of the present invention.

Referring to FIG. 5, a tracking coil assembly 300 for use with an intrabody medical device 80, according to some embodiments of the present invention, is illustrated. The tracking coil assembly 300 includes a bobbin or spool 302 around which a tracking coil 80c is wound, as illustrated. The spool 302 is formed from MRI-compatible material. In some embodiments, the tracking coil 80c may include between about 1 and 20 turns, and typically between about 3 and 10 turns. The tracking coil 80c may include about six turns or less of conductive wire (insulated or non-insulated). An exemplary wire diameter is about 0.003 inches. However, conductive wire having other diameters may also be used. The spool 302 includes a central lumen 304 through which pass-through cables associated with an intra-body device (not shown) extend. Although two pass-through cables $C_1$, $C_2$ are shown extending through the spool lumen 304 in the illustrated embodiment, it is understood that there may be various numbers of such cables. The pass-through cables may include various electrical cables as well as mechanical cables, e.g., cables for facilitating articulation of a device 80, etc. A coaxial cable 306 electrically connected to the tracking coil 80c extends through a wall 308 of the spool 302 via a passageway 310, and through a wall 312 of the spool 322 via a passageway 311, as illustrated. The coaxial cable 306 includes an outer conductor 306a connected to one end of the tracking coil 80c and an inner conductor 306b connected to the opposite end of the tracking coil 80c, as illustrated.

The illustrated tracking coil assembly 300 also includes an RF shield 320 positioned in end-to-end, adjacent, spaced-apart relationship to the tracking coil spool 302. The RF shield 320 is configured to impede RF coupling along a conductive element(s) inserted within the RF shield 320. The illustrated RF shield 320 includes a bobbin or spool 322 formed from MRI-compatible material that is configured to accommodate a plurality of turns of the coaxial cable 306 connected to the tracking coil 80c. For example, the spool 322 may have a length sufficient to accommodate twenty (20) turns of the coaxial cable 306. However, the RF shield spool 322 may have various lengths and can accommodate any number of turns of coaxial cable 306. Embodiments of the present invention are not limited to a particular spool length.

The spool 322 includes a central lumen 324 through which pass-through cables $C_1$, $C_2$ associated with an intra-body device extend, as illustrated. $C_1$, $C_2$ are intended to represent all leads, cables, wires, fluid pathways and other components that may be associated with intra-body devices. In addition, as illustrated in FIG. 5, the tracking coil spool 302 and the RF shield spool 322 may be maintained in adjacent, spaced-apart relationship via a spacer 324, such as, a polymeric spacer tube that is MRI-compatible, for example.

Figure 6:
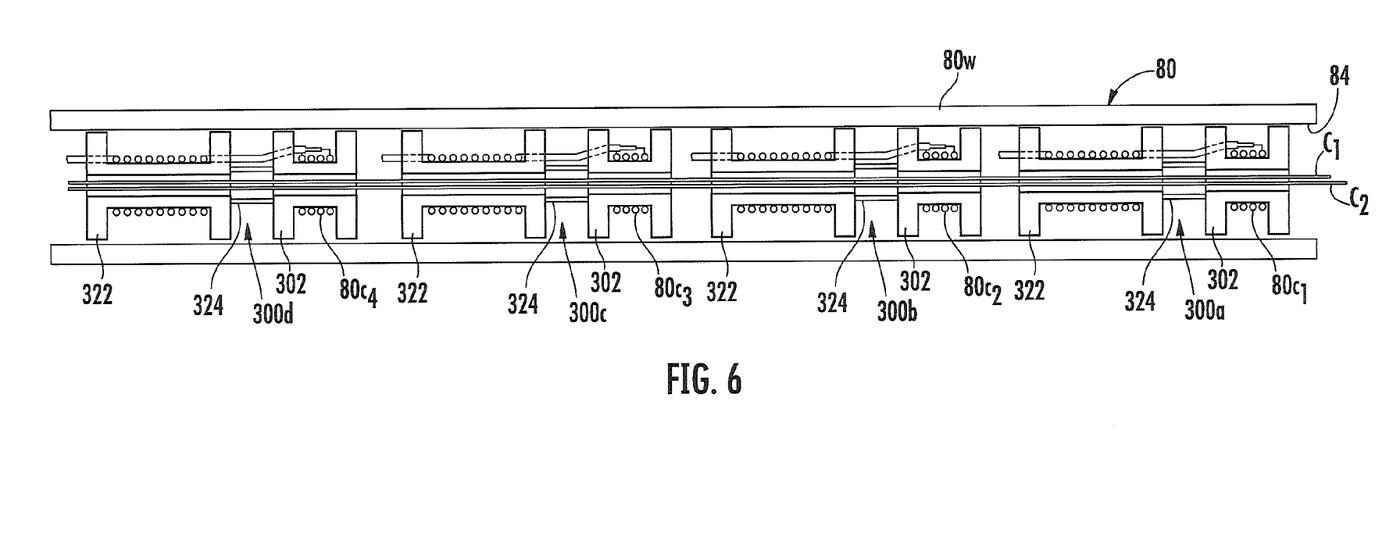
FIG. 6 is a side section view of an intrabody medical device incorporating a plurality of the tracking coil assemblies of FIG. 5, according to some embodiments of the present invention.

Referring to FIG. 6, an intrabody medical device 80 incorporating a plurality of the tracking coil assemblies 300 of FIG. 5 is illustrated. The device 80 includes four tracking coil assemblies 300a, 300b, 300c, 300d in end-to-end adjacent relationship. Each respective tracking coil assembly includes a respective tracking coil 80c, tracking coil spool 322 and RF shield 320, as described above. In the illustrated embodiment, the tracking coil assemblies 300a, 300b, 300c, 300d are located within the lumen 84 of the device 80. In some embodiments, one or more portions of the tracking coil assemblies 300a, 300b, 300c, 300d may be embedded within the wall 80w of the device 80. For example, one or more portions of the spools 302, 322 may be embedded within the wall 80w of the device 80.

The tracking coil assemblies 300a, 300b, 300c, 300d may be spaced apart in various configurations. For example, the first and second tracking coil assemblies 300a, 300b may be relatively close to each other and the third and fourth tracking coil assemblies 300c, 300d may be spaced apart from the first and second tracking coil assemblies 300a, 300b, etc. Polymeric spacer tubes of various sizes and/or configurations may be utilized to maintain the desired space between adjacent tracking coil assemblies.

In some embodiments, the intrabody device 80 (FIGS. 1 and 2) is configured to allow for safe MRI operation so as to reduce the likelihood of undesired deposition of current or voltage in tissue (inhibit or prevent undesired heating). The device 80 can include RF chokes such as a series of axially spaced apart Balun circuits or other suitable circuit configurations. See, e.g., U.S. Pat. No. 6,284,971 and PCT Publication No. WO 2012/112829, the contents of which are hereby incorporated by reference as if recited in full herein, for additional description of RF inhibiting coaxial cable that can inhibit RF induced current. The conductors connecting electrodes or other components on or in the catheter (or other interventional device) can also include a series of back and forth segments (e.g., the lead can turn on itself in a lengthwise direction a number of times along its length) and/or include high impedance circuits. See, e.g., U.S. Pat. Nos. 7,561,906 and 8,055,351, as well as U.S. Patent Application Publication No. 2008/0243218 and PCT Publication No. WO 2008/115383, the contents of which are hereby incorporated by reference as if, recited in full herein.

Curve Position Encoding Catheter Handle

Figure 7:
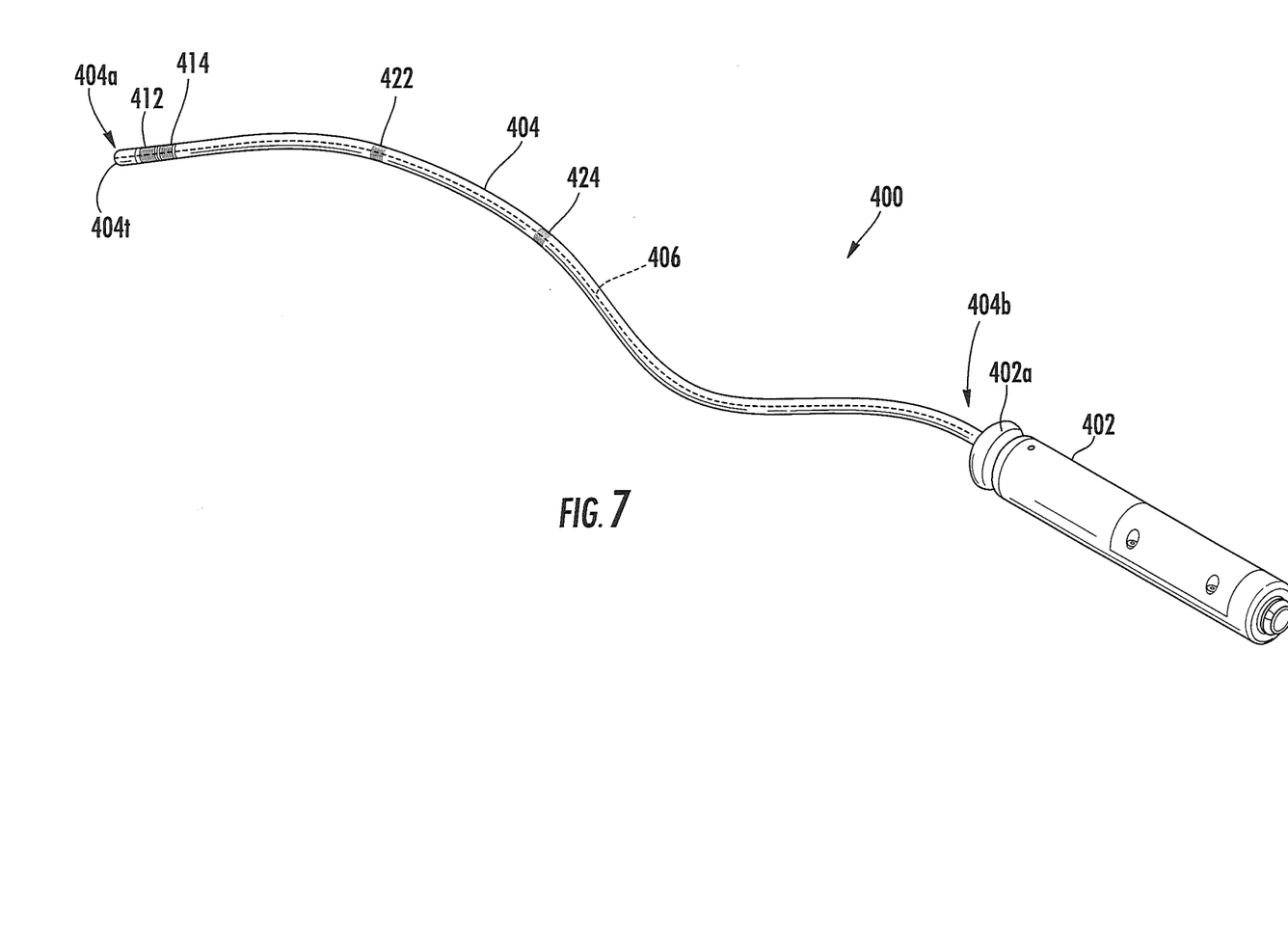
FIG. 7 is a perspective view of an exemplary intrabody medical device, according to some embodiments of the present invention.

Referring now to FIG. 7, an intrabody medical device 400, according to some embodiments of the present invention, is illustrated. The illustrated device 400 is a flexible (steerable) catheter that includes a handle 402 and an elongated flexible housing or shaft 404 with opposite distal and proximal end portions 404a, 404b, respectively. A pair of tracking members individually identified as 412, 414, and which are equivalent to coils 82c of FIGS. 1-2, are positioned upstream from the catheter tip 404t, as illustrated. A second pair of tracking members individually identified as 422, 424, and which are equivalent to coils 82c of FIGS. 1-2, are positioned upstream from the first pair of tracking members 412, 414, as illustrated. The proximal end portion 404b of the catheter shaft 404 is operably secured to the handle 402. The catheter shaft 402 is formed from flexible, bio-compatible and MRI-compatible material, such as, for example, polyester or other polymeric materials. However, various other types of materials may be utilized to form the catheter shaft 404, and embodiments of the present invention are not limited to the use of any particular material.

Figure 8A:
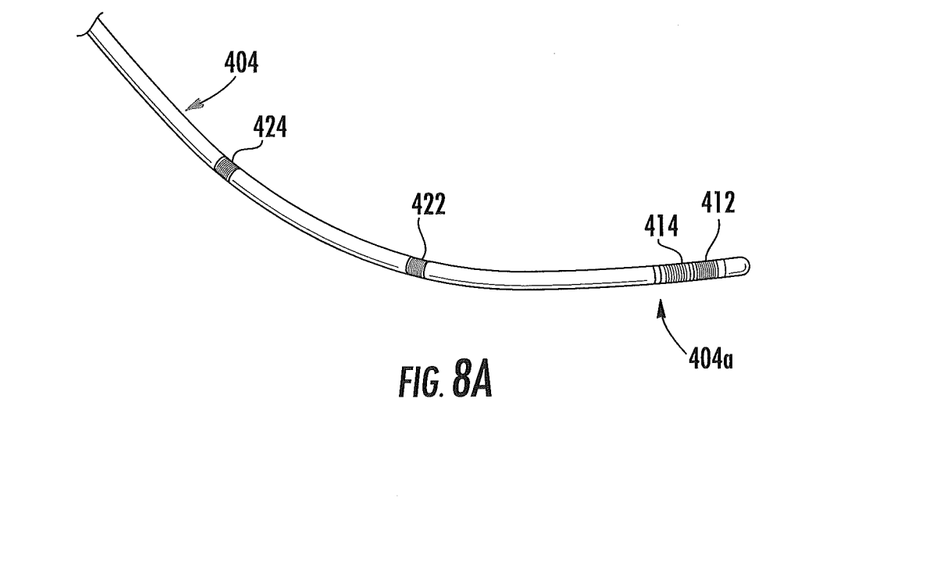
FIG. 8A is a partial perspective view of the distal end portion of the catheter of FIG. 7.
Figure 8B:
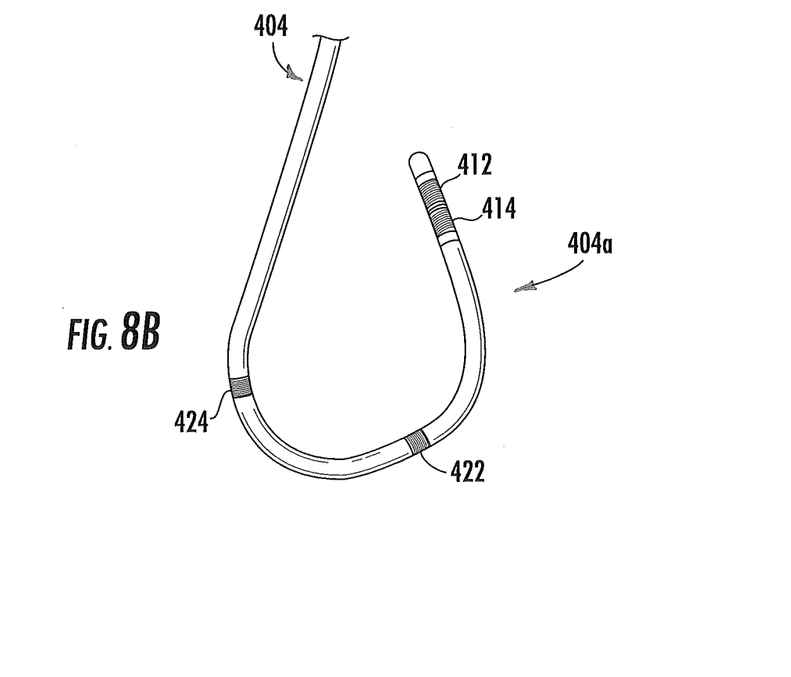
FIG. 8B illustrates the distal end portion of the catheter of FIG. 7 in an articulated configuration, according to some embodiments of the present invention.

FIGS. 8A and 8B illustrate the distal end portion 404a of the catheter shaft 404 of FIG. 7 in a substantially elongated configuration (FIG. 8A) and in an articulated and/or curvilinear configuration (FIG. 8B), respectively. The ability to articulate and/or bend and/or deform the distal end portion 404a facilitates positioning the catheter tip 404t at desired locations (e.g., within a heart) during a procedure. The term "articulation", as used herein, is intended to include all ways that the catheter tip 404t can be moved or modified or shaped (e.g., curvilinear movement, deforming movement, etc.).

Figure 10A:
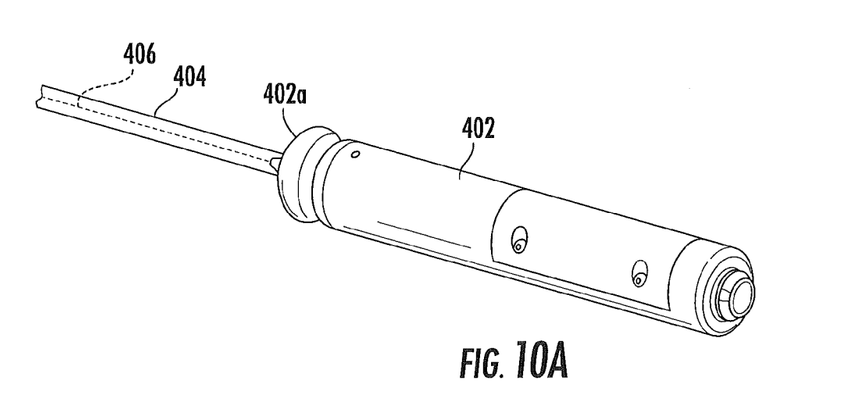
FIG. 10A is a perspective view of the device of FIG. 7 with an actuator in a retracted position.
Figure 10B:
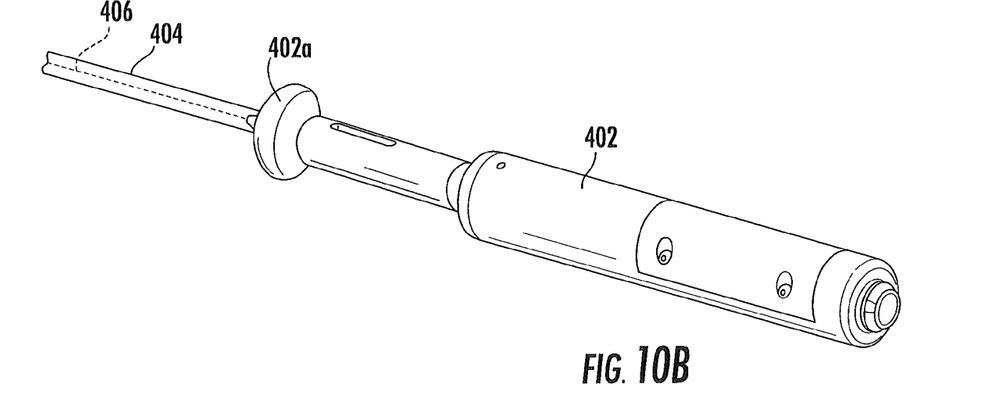
FIG. 10B is a perspective view of the device of FIG. 7 with an actuator in an extended position.

In the illustrated embodiment, articulation of the catheter distal end portion 404a is achieved by movement of a pull wire 406 (FIG. 7) disposed within the catheter shaft 404 and that extends from the catheter tip 404t to the catheter handle 402. Movement of the pull wire 406 is accomplished via an actuator 402a associated with the handle 402. The handle actuator 402a is connected to the pull wire 406 and can articulate the catheter shaft distal end portion 404a. FIG. 10A illustrates the actuator 402a of the device 400 of FIG. 7 in a retracted position and FIG. 10B illustrates the actuator 402a of the device 400 of FIG. 7 in an extended position. Movement between the retracted and extended positions articulates the catheter shaft distal end portion 404a.

Embodiments of the present invention, however, are not limited to the illustrated actuator 402a. Actuator 402a may be any of various types of devices (e.g., levers, pistons, thumb sliders, knobs, etc.).

Figure 9:
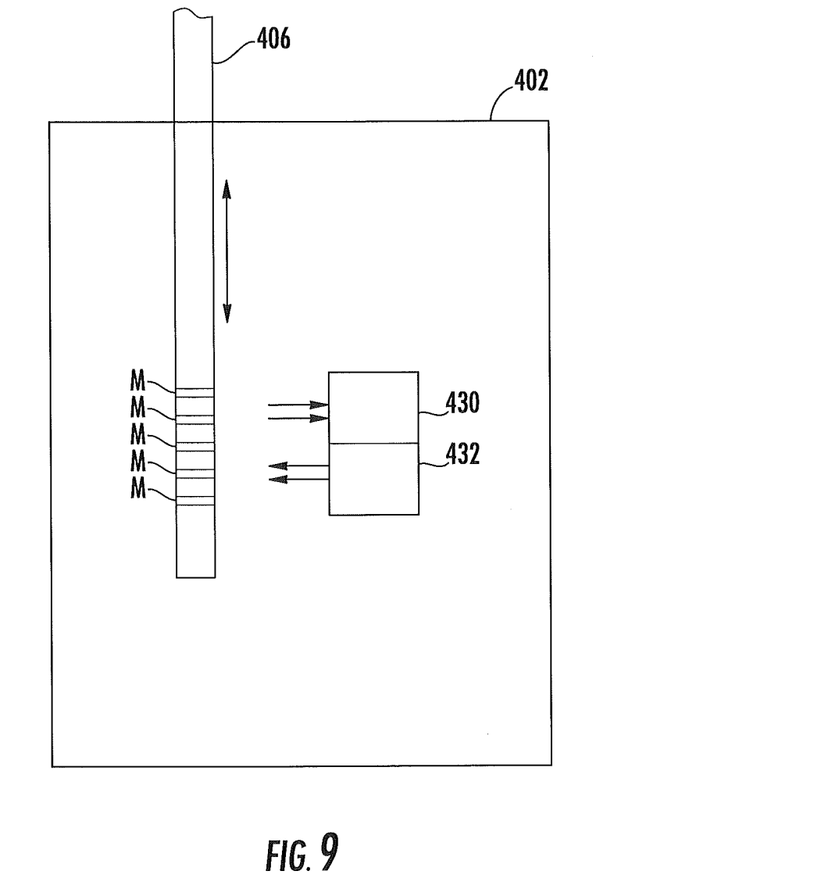
FIG. 9 is a schematic illustration of the handle of the catheter of FIG. 7 illustrating markings on the pull wire and an optical detector, according to some embodiments of the present invention.

As the catheter handle actuator 402a is manipulated in a certain way, the pull wire 406 is pulled or pushed which results in a change in the shape of the distal end 404a of the catheter. The pull wire 406 includes a plurality of markers M (FIG. 9) on the pull wire 406 that can be electronically perceived at a fixed location/region/zone or point within the catheter handle (e.g., via optical sensing, etc.). By monitoring movement of these markers M via a detector or other similar device associated with the handle 402, the deflectable catheter handle will produce data that indicates, at any point in time, how much the pull wire 406 has moved in relation to a fixed point on the catheter handle 402. This measurement might be readout in +/− millimeters, for example, on a display (remote and/or onboard). This data is referred to herein as "pull wire position data" or PWPD.

A processor 60p associated with an MRI scanner 10S (FIG. 1) can take the PWPD and process the data via an algorithm that defines or reconstructs the 3D position of a distal length of the catheter (e.g., 10 centimeter length of catheter). As known in the art, data points used to define the 3D position of the catheter may include single points tracked in 3D along the length of the catheter, or signals from an antenna shaft along the length of the catheter. These data points may be presented as projection images for example.

Combining the PWPD with other data points (e.g., information from the tracking coils 412, 414, 422, 424 located on the catheter shaft 404 and/or from loop or loopless antenna(s) located along the catheter shaft 404) relating to the position of the catheter distal end portion 404a may increase speed and accuracy of determining the location of the distal end portion 404a. For example, if the PWPD indicates that the pull wire 406 has been pulled back by 1 centimeter, then the processor 60p can determine that the distal portion 404a of the catheter shaft 404 has been deflected into a "C" shape. By adding this predicted "C" shape information from time period "A" into the algorithm, and combining it with 3D information about the catheter (i.e. from tracking coils and/or antenna signal/s) also from time period "A", the processor 60p will be able to better and/or more quickly define or reconstruct the 3D position of the distal length of the catheter.

In some embodiments, an optical reader 430 and optical emitter 432 are disposed within the catheter handle 402. The optical reader 430 is configured to read indicia or marks along a length of the pull wire 406. A processor associated with an MRI scanner 10S (FIG. 1) receives the PWPD from the optical reader and combines this with other data points relating to the position of the catheter distal end portion 404a, as described above.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. An MRI-compatible intrabody device, comprising:
   an elongated flexible shaft having a distal end portion, and an opposite proximal end portion;
   an electrical connector interface configured to be in electrical communication with an MRI scanner; and
   a tracking coil assembly positioned within the shaft, the tracking coil assembly comprising:
   a first spool having opposing first and second end walls;
   a tracking coil wound around the first spool between the opposing first and second end walls;
   a second spool having opposing third and fourth end walls, wherein the second spool is in end-to-end relationship with the first spool such that the second and third end walls are in adjacent, spaced-apart relationship; and
   a coaxial cable wound around the second spool, wherein an outer conductor of a distal portion of the coaxial cable is connected to one end of the tracking coil, wherein an inner conductor of the distal portion of the coaxial cable is connected to an opposite end of the tracking coil, and wherein a proximal end of the coaxial cable is connected to the electrical connector interface and configured to electrically connect the tracking coil to an MRI scanner.

2. The device of claim 1, wherein the first and second spools comprise MRI-compatible material.

3. The device of claim 1, wherein the tracking coil is a 1-10 turn solenoid coil.

4. The device of claim 1, wherein a distance between the first and second walls is between about 0.25 mm and about 4 mm.

5. The device of claim 1, wherein coaxial cable is wound around the second spool between about twenty (20) and about two-hundred (200) times.

6. The device of claim 1, wherein a free end of the coaxial cable extends through respective apertures in the second and third end walls.

7. The device of claim 1, comprising a spacer positioned between the first and second spools.

8. The device of claim 1, wherein the first and second spools each comprise a lumen extending longitudinally therethrough.

9. The device of claim 1, wherein the tracking coil assembly comprises a plurality of first and second spools in spaced-apart relationship within the shaft, wherein a tracking coil is wound around each respective first spool between the opposing first and second end walls, wherein a coaxial cable is wound around each respective second spool, wherein an outer conductor of a distal portion of each coaxial cable is connected to one end of a respective tracking coil, wherein an inner conductor of the distal portion of each coaxial cable is connected to an opposite end of each respective tracking coil, and wherein a proximal end of each of the plurality of coaxial cables is connected to the electrical connector interface and configured to electrically connect the respective tracking coils to an MRI scanner.

10. The device of claim 1, wherein the flexible shaft has a size that is between about 5 French to about 12 French.

* * * * *